(12) United States Patent
Fischer et al.

(10) Patent No.: US 10,330,613 B2
(45) Date of Patent: Jun. 25, 2019

(54) METHOD AND DEVICE FOR THE AUTOMATABLE DETERMINATION OF THE LIMIT OF QUANTIFICATION AND THE RELATIVE ERROR WHEN QUANTIFYING THE CONCENTRATION OF A SUBSTANCE TO BE INVESTIGATED IN A TEST SAMPLE

(71) Applicant: Bruker BioSpin GmbH, Rheinstetten (DE)

(72) Inventors: Christian Fischer, Rheinstetten (DE); Carsten Kuhl, Karlsruhe (DE); Kimberly Colson, Westford, MA (US)

(73) Assignee: BRUKER BIOSPIN GMBH, Rheinstetten (DE)

( * ) Notice: Subject to any disclaimer, the term of this patent is extended or adjusted under 35 U.S.C. 154(b) by 302 days.

(21) Appl. No.: 15/297,637

(22) Filed: Oct. 19, 2016

(65) Prior Publication Data
US 2017/0108454 A1  Apr. 20, 2017

(30) Foreign Application Priority Data
Oct. 19, 2015  (DE) ........................ 10 2015 220 322

(51) Int. Cl.
G01N 24/08  (2006.01)
G01R 33/46  (2006.01)

(52) U.S. Cl.
CPC ......... *G01N 24/08* (2013.01); *G01R 33/4625* (2013.01)

(58) Field of Classification Search
None
See application file for complete search history.

(56) References Cited

U.S. PATENT DOCUMENTS
2015/0247813 A1  9/2015  Fischer

FOREIGN PATENT DOCUMENTS
DE  102014203721 A1  9/2015

OTHER PUBLICATIONS

Zorn et al., "Evaluation of Approximate Methods for Calculating the Limit of Detection and Limit of Quantification" Environ. Sci. Technol. 1999, 33, 2291-2295.*

(Continued)

*Primary Examiner* — John C Kuan
(74) *Attorney, Agent, or Firm* — Edell, Shapiro & Finnan, LLC

(57) ABSTRACT

A spectroscopic method for calculating a limit of quantification and a relative error includes: 1. selecting an error function F(C); 2. providing a blank spectrum; 3. recording a reference spectrum with a signal content of the substance being investigated; 4. determining start concentrations; 5.a. multiplying the reference spectrum with the signal content of the substance by a factor; 5.b. adding the resulting spectrum to the blank spectrum and determining the corresponding concentration of the substance and calculating the corresponding relative error; 6. iteratively adapting parameters of the selected error function F(C): recording a measurement spectrum of the test sample and determining the concentration of the substance being investigated using 5.b. and comparing with the calculated limit of quantification and calculating the relative error by applying the error function from step 6.

12 Claims, 4 Drawing Sheets

(56) References Cited

OTHER PUBLICATIONS

Shrivastava et al., "Methods for the determination of limit of detection and limit of quantitation of the analytical methods" Chronicles of Young Scientists, vol. 2, Issue 1, Jan.-Mar. 2011.*
Green, "A Practical Guide to Analytical Method Validation" Analytical Chemistry News & Features, May 1, 1996.*
Chandran et al., "Comparison of various international guidelines for analytical method validation" Pharmazie 62: 4-14 (2007).*
Schoenberger T. et al., "Guide to NMR Method Development and Validation—Part I: Identification and Quantification", Technical Report No. 01/2014, EUROLAB General Secretariat, May 2014, pp. 1-20.
Armbruster et al., "Limit of Blank, Limit of Detection and Limit of Quantitation", Clin BioChem Rev, vol. 29, Aug. 2008, 6 pages.
Marchetto A. et al., "Limit of Detection (LOD) and Limit of Quantification (LOQ) estimation and use in the chemical lab", Life+ FutMon—Working Group on QA/QC in Laboratories Meeting of the Heads of the Laboratories, Oct. 2009, 36 pages.
Alankar S. et al., "Methods for the determination of limit of detection and limit of quantitation of the analytical methods", Chronicles of Young Scientists, vol. 2 Issue 1, 2011, pp. 21-25.
Ermer, J. et al., "Method validation in pharmaceutical analysis", Wiley-VCH, Weinheim, 2005, pp. 101-119.
Muncey, H. et al., "MetAssimulo: Simulation of realistic NMR metabolic profiles", BMC Bioformatics 2010, 11:496.
BRUKER Software "AssureNMR", retrieved from the internet at https://www.bruker.com/fileadmin/user_upload/8-PFD-Docs/magneticresonance/events_NMR/ENC2015/Posters/17_ENC15_Assurelores.pdf, sumitted 2016.

* cited by examiner

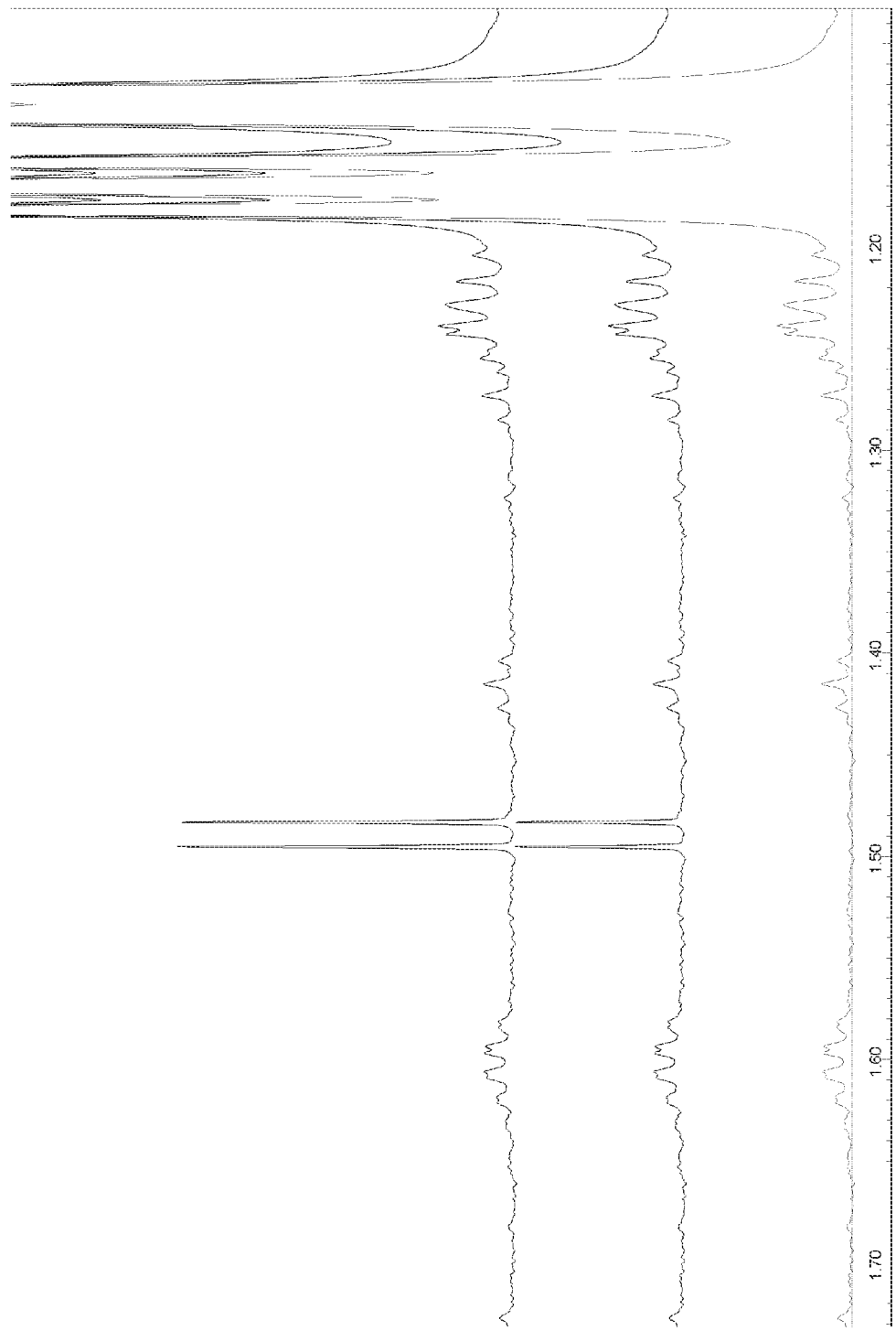

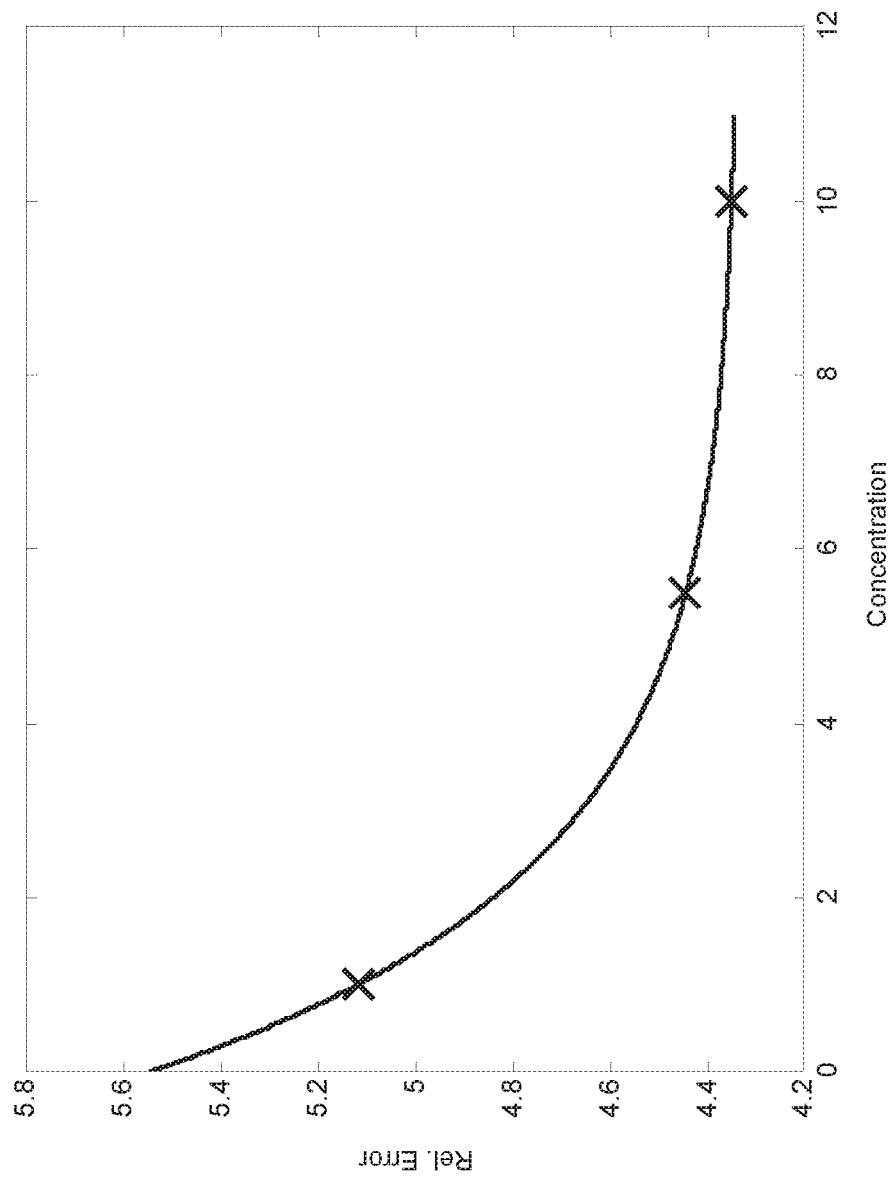

METHOD AND DEVICE FOR THE AUTOMATABLE DETERMINATION OF THE LIMIT OF QUANTIFICATION AND THE RELATIVE ERROR WHEN QUANTIFYING THE CONCENTRATION OF A SUBSTANCE TO BE INVESTIGATED IN A TEST SAMPLE

CROSS REFERENCE TO RELATED APPLICATIONS

This application claims foreign priority under 35 U.S.C. § 119(a)-(d) to German Application No. 10 2015 220 322.0 filed on Oct. 19, 2015, the entire contents of which are hereby incorporated by reference.

FIELD OF THE INVENTION

The invention relates to a spectroscopic method generally, and more specifically, to a spectroscopic method for determining the limit of quantification (LOQ) and for determining the relative error when quantifying the concentration of a substance to be investigated in a test sample, wherein the limit of quantification specifies the concentration of the substance at which the relative measuring error becomes less than a specified value $E_B$, and wherein, in a measured spectrum, an intensity is determined as a function of a position with a signal component which can be ascribed to the substance.

BACKGROUND

A frequent objective in quality assurance in numerous industrial processes, or also in research and medical diagnostics, is the quantitative examination of the composition of a collected sample, in particular the determination of the concentration of a certain substance in the sample. In order to determine the concentration of a substance in a sample, the substance contained in the sample can be quantitatively converted with a reagent, for example until a color change of an added indicator indicates the end of the conversion reaction, while the quantity of the added reagent is tracked. However, such conventional chemical methods are quite laborious and have recently been replaced in large part by spectroscopic methods. With spectroscopic methods, the interaction of the substance in the sample with an investigatory radiation is used to determine the concentration. Such a spectroscopic method is disclosed for example in DE 10 2014 203 721 A1 (=Reference [2])

A powerful spectroscopic method of quantity analytical chemistry is nuclear magnetic resonance (NMR) spectroscopy. Here, typically, in one-dimensional NMR spectroscopy, the nuclear spins in the sample are aligned in a strong, static magnetic field, and the nuclear magnetization is rotated through 90° with a high-frequency pulse. The high-frequency response of the sample is then recorded as a function of time (referred to as a free induction decay (FID) signal). A frequency spectrum of the sample containing characteristic peaks for the individual constituents of the sample can be obtained from the time signal by Fourier transformation, wherein the individual peaks of the constituents overlap to a greater or lesser extent.

The intensity of the peaks of the individual constituents of the sample is basically proportional to the concentration of the associated constituent in the sample. However, due to the overlapping of a multiplicity of peaks in a spectrum, it is often not easy to quantitatively determine the signal component belonging to a particular substance. This not only applies to NMR, but also to other spectroscopic methods such as infrared (IR) spectroscopy or x-ray spectroscopy (x-ray fluorescence or x-ray absorption).

It is also known to identify the individual peaks associated with a substance and to determine the relative positions, intensities, line widths and line forms in a reference spectrum of the substance to be quantified. The peaks can then be fitted to the measured spectrum of the sample and, in turn, integration under the fitted peaks can be carried out in order to quantify the signal content of the substance. This so-called multiplet approach is implemented, for example, in the "Chenomx NMR Suite" spectral analysis software from Chenomx Inc., Edmonton, Alberta, Calif.

The limit of quantification and the error in the quantification in the determined concentration of a substance to be investigated are very important for assessing the results when evaluating spectra.

The limit of quantification (LOQ) is the lowest concentration of a substance in a measuring sample which can be quantitatively determined with a defined precision, e.g. with the relative error. Measuring results are usually only declared when this value is reached.

The limit of detection (LOD) is the lowest concentration of a substance in a measuring sample at which the substance can still be reliably detected. For example, the limit of detection can be determined by choosing the concentration above which the determined concentration becomes >0. All values below this concentration are designated as "undetectable."

The integral of the signal of a substance is generally directly proportional to the concentration. In optical spectroscopy (IR, ultraviolet (UV), visual), this fact is described by the Beer-Lambert law; the behavior is similar in NMR spectroscopy.

Due to the linearity of signal and concentration, it is possible to produce artificial mixtures by adding spectra (see, for example, Reference [3]). The addition of a defined quantity of a substance to a mixture is referred to as "spiking." If instead of the actual addition of a substance, a spectrum of the substance with a defined integral is added to a spectrum of a mixture, this is referred to as "electronic spiking."

A substance in a spectrum can be quantified using different known methods, such as:
1. Integration of a region by summing the intensity values.
2. Identification of the individual signals with subsequent summation of the individual integrals. and
3. Adaptation of a line form ("model") to an experimental signal (see Reference [2]).

The above methods 2 and 3 use iterative algorithms to adapt the individual parameters, e.g., Levenberg-Marquardt or Gauss-Newton. Internally, the least squares method is normally used in each iteration step to calculate the deviation between model and experiment. This method has proved useful in practice. In addition, for practical reasons (above all computation time), a tolerance is assumed. If the values change during the iteration by less than the specified tolerance, the calculation is terminated. For example, the iteration is terminated if the change lies within the tolerance during the calculation of the target accuracy.

Quantifications according to methods 2 and 3 provide more accurate results but require an appreciable amount of computation time. It is therefore important to limit the number of steps necessary in a quantification as much as possible.

The accuracy of the quantification result depends on many factors. One of these factors is the spectral background which, among other things, includes:

Noise.

Other signals in the region which overlap with the substance.

These effects play an ever decreasing role with increasing substance concentration, since the relative error becomes smaller.

Usual methods for determining LOQ, LOD (according to Reference [1]) include:

Visual definition.

Signal/noise ratio: LOD: 2-3*noise level, LOQ: 10*noise level.

Standard deviation in a spectrum of a blank sample according to Equation 1.

Calculation based on the calibration line (e.g. linear regression) at low concentration according to the following equation:

LOD/LOQ=$F$*SD/$b$, where (Equation 1)

F: Factor, e.g. for LOD, F=3.3; for LOQ, F=10.0. Accepted values in practice [1].

SD: Standard deviation. Examples according to Reference [1] include:

Values in the noise region in the blank spectrum.

Residues of linear regression of the calibration line.

Slope of the calibration line/Values in the spectrum.

The present invention builds on the prior art according to a technique used in the Bruker "AssureNMR" software (see Reference [4]), which uses the following steps to determine LOQ:

1. First, a quantification is carried out at concentration 0, that is to say with the pure, "blank" spectrum. If the substance is not identified, the relative error in this case is set to "infinity," as the expected concentration is zero.

2. A start concentration is determined. For practical reasons, the concentration "1" is assumed regardless of the units. The sample spectrum is then calculated and subsequently quantified. If the quantification is not successful, the concentration is multiplied by a factor of 10 until a concentration >0 and an error less than the aimed-for relative error are obtained.

3. Iteration using the binary search method:
    a. Determination of the current concentration=Mean value of greatest concentration>max. relative error and lowest concentration<max. relative error.
    b. Electronic spiking+quantification.
    c. Determination of the relative error.
    d. Distance between greatest concentration>max. relative error and lowest concentration<max. relative error.
    e. Is this distance less than the required accuracy? Then terminate.

4. LOQ is the lowest concentration <max. relative error within the allowed tolerance.

The number of iterations can become very high; to a certain extent the search is carried out blind. The method requires a large number of iteration steps and is relatively slow due to the many quantification steps to be carried out.

In addition, heretofore, there has been no way of estimating the accuracy of quantification results for the currently determined concentration. The accuracy as a function of the concentration has not previously been estimated.

Known methods and conventional solutions therefore have at least the following disadvantages or shortcomings:

It is impossible or nearly impossible to determine the error for a given concentration.

Concentration series (electronic and mechanical) must be set manually.

Overly simple formula: Multiplying the signal/noise ratio by a single factor does not take into account the chemical background: Signals in the region can, however, be due to other substances, possibly in low concentration.

Determination of LOQ at different specified accuracy values $E_B$ with simply a one-off calculation of the model function. In practice, two limits of quantification are frequently specified, for example 1% and 5%.

SUMMARY

The present invention provides a simplified, automatable method for calculating the limit of quantification and the possibility of quantitatively estimating the error of a determined concentration of a substance in a sample taking into account the chemical background.

The method of the present invention includes the following steps or sequences of steps:

1. Selection of an error function F(C) which specifies how the relative measuring error E changes with the concentration C of the substance and is dependent on n parameters;

2. Provision of a blank spectrum;

3. Recording of a reference spectrum with/having the signal content of the substance to be investigated;

4. Determination of n start concentrations $C_i^0$ (i=1 ... n) of the substance;

5. Carrying out the following individual steps for each start concentration $C_i^0$:
    a) Multiplication of the reference spectrum having the signal content of the substance by a factor which is chosen such that the signal content corresponds to the concentration of the substance;
    b) Addition of the spectrum from individual step 5a) to the blank spectrum from method step 2. and determination of the concentration of the substance $C_{step}$ resulting from the addition and calculation of the relative error $E_{step}$;

6. Iterative adaptation of the parameters of the selected error function F(C) by using the following intermediate steps:
    a) Determination of the n parameters of the error function F(C) with the help of/based on the previously determined relative error $E_{step}$ from individual step 5b) for each corresponding concentration $C_{step}$;
    b) Determination of a new concentration value $C_x$, wherein the error function F(C) with the parameters determined in intermediate step 6a) is used to calculate the concentration value $C_x$ at the specified value of the selected relative error $E_B$;
    c) Carrying out individual steps 5a) and 5b) for the concentration value $C_x$ from/determined in intermediate step 6b) with calculation of a further concentration $C_{step2}$ and further corresponding relative error value;
    d) Repetition of intermediate steps 6a) to 6c) with, in addition, the values of the further concentration $C_{step2}$ and the further relative error calculated from intermediate step 6c) if, for the concentration value obtained from intermediate step 6c), the value $E_B$ of the relative error E corresponding to the limit of quantification LOQ does not lie within a specified tolerance range;

7. Recording of a measurement spectrum of the test sample and determination of the concentration C of the substance to be investigated with the same method as in individual step 5b) using the measurement spectrum of the test sample and comparison of the concentration C with the limit of quantification and calculation of the relative error E by applying the error function from method step 6.

In accordance with the method, the error function describes the error as a function of the concentration. Concentrations are either 0 or positive. With very small concentrations, the error becomes infinite, particularly when the substance is not detected and therefore the calculated concentration is 0. The function therefore decreases steeply at the beginning and then becomes flatter. As the relative error becomes ever smaller with increasing concentration, the function is a monotonically decreasing function. Exponential functions fulfill these conditions and have been shown to be suitable in testing.

The concentration is given by the signal intensity peak with the given hardware. The concentrations are selected in an expected range. In the exemplary embodiment, a value (e.g. 1 mmol) is assumed; if this is not meaningful, it is multiplied by a factor 10 until a meaningful value is obtained. From this, half is then taken, etc.

Method step 5b) is non-trivial when performed in the present context and requires substantial computation power. The sought-after signals are fitted into the spectrum for a given concentration. For the subsequent part of method step 5b) "Determination of the concentration $C_{step}$," there are different options for fitting the pure spectrum in the mixed spectrum.

Even more demanding is the method step 6a) "Determination of the n parameters of the error function." This step comprises a mathematical method for matching the concentration error curve, a method using the least error squares being preferred here. But in Step 6a) too, different paths lead to the desired result.

If necessary, further concentration values can be determined in an additional Step 8 to better match the model function. This minimizes the error of the model function.

An additional Step 9 can also be beneficial in practice, and may include measurement and quantification of one or more new spectra using the following further iteration steps:
  a) Recording of a further measurement spectrum of the test sample to be investigated which also contains the sought-after measuring substance;
  b) Quantification as in Step 5b);
  c) Calculation of a relative error component of the spectral background by applying the model function.

Henceforth, the following are made possible with the help of the present invention:
  a) a determination of the limit of quantification (or limit of detection) when quantifying a substance in a sample.
  b) an estimation of the error using the spectral background (signal/noise) at a calculated concentration.
  c) a determination of the limit of quantification during the statistical analysis of a sample with answers to the questions "From what concentration of the substance is the sample classified as an outlier?," or "In which concentration range is the sample classified as "in model"?"

The basic idea of the solution according to the invention described above enables considerable advantages to be achieved:
  a) The independence of the relative error of the concentration is determined as a mathematical function (model function). This enables LOQ values to be calculated for different accuracies (e.g. 1% error, 5% error). This model is determined by simulations (electronic spiking). Continuous determination of the mathematical function while a specified LOQ value is being determined enables the number of simulations to be minimized.
  b) Determination of the error component using the spectral background by applying the model function with the currently determined concentration.

Summaries of variants/embodiments of the invention are now described.

As the relative error becomes smaller with increasing concentration, as a rule, the function should be a monotonically decreasing function. Exponential functions fulfill these conditions and have been shown to be suitable in testing. An exponential term $(f(x)=a*exp(b*x)+c)$ in the function is usually sufficient, that is to say an error function $F(C)=a*exp(b*C)+d$, where C represents the concentration and $F(C)$ the relative error.

Even more accurate results can be achieved with two exponential terms $(f(x)=a*exp(b*x)+c*exp(d*x)+e)$.

In preferred method variants, a spectrum of a blank sample which does not contain the substance, or a theoretical noise spectrum or a spectrum of a test sample to be investigated which also contains the sought-after measuring substance is provided in method step 2., wherein the concentration of the substance in the test sample is already known and the calculated signals of the substance are subtracted from the spectrum.

A plurality of blank spectra can also be provided in method step 2., wherein, as the current error, the maximum of the individual deviations or some other error quantile is used to optimize the error function.

Advantageously, the positions of the signal components can be varied, in particular by shifting the reference spectrum between the individual steps 5a) and 5b), preferably by some ppm. In NMR spectroscopy for example, the signal positions typically vary with the solvent, the pH value and other substances in the sample.

Preferred are variants of the method according to the invention, in which a dedicated error function and therefore the limit of quantification is determined as a function of position for each signal position.

When using a plurality of blank samples, the blank spectra can be classified in advance, wherein an error function is determined for each class in order to enable a class-specific processing of new samples.

In method step 3., the signal components of the substance to be investigated can be measured using a measured reference spectrum or by a simulation.

A further class of advantageous method variants is distinguished in that the errors from the adaptation of the experimental values are added to the error function in the value of the calculated error due to the background.

Instead of an electronic addition of signal components to the blank spectra in the individual steps 5a) and 5b), the substance to be investigated can also be mixed and measured with the blank samples.

For determining the error of new samples, the error function can be divided into different concentration ranges in order to guarantee a more accurate adaptation, wherein, particularly for higher substance concentrations, a linear function is used instead of an exponential function.

Method variants, in which, instead of quantifying the concentration of a measuring substance in a test sample, the method is used to determine the limit of quantification of statistical models, also fall within the framework of the present invention, wherein, instead of relative concentration errors, statistical parameters are used in univariate and multivariate statistics—such as the distance from the mean value. Here, for example, it is a matter of determining the concentration of the substance above or below which a sample is identified as an "outlier." This can also be applied to a concentration range: too much of the substance means "outlier," too little likewise means outlier.

In variants of the method according to the invention, the limit of detection (LOD) can also be calculated instead of the limit of quantification (LOQ), wherein the limit of detection specifies the concentration above which the substance to be investigated can be identified.

The measured spectrum can be pre-processed before the optimization algorithm is started, in particular using baseline correction or phase correction. Likewise, the measured reference spectrum can be pre-processed before the optimization algorithm is started, in particular to be assigned narrow spectral lines (peaks).

Particularly preferred is a method variant in which the method is used in NMR spectroscopy, in particular one-dimensional NMR spectroscopy. Here, the measured spectrum is obtained from an FID signal of the sample by Fourier transformation. The position information in the spectrum is then the frequency, usually specified in ppm of a chemical shift.

A method variant is also possible in which the method is used in optical spectroscopy, in particular IR spectroscopy, or x-ray spectroscopy or mass spectroscopy. As a rule, the position information will then be a wavelength. Here too, the simple steps of the method can be easily applied without an expert in spectral analyses. Furthermore, a method variant, in which the sample is a liquid sample or a solid sample, in particular a powdery sample, is preferred. Severe line broadening, which can be easily handled by the method according to the invention, occurs with liquid samples, particularly in NMR. However, the invention is also easy to apply to solid samples.

It is to be noted that multidimensional variables also come into consideration within the framework of the invention (for example, in so-called 2-dimensional NMR spectroscopy).

A spectroscopy apparatus, designed for automatically carrying out the method according to the invention, particularly wherein the spectroscopy apparatus comprises a measuring unit for recording the measured spectrum of the sample and/or the measured reference spectrum of the substance, also falls within the framework of the present invention. The method according to the invention is particularly well-suited to be performed automatically. Conventional computer systems with appropriate programming and suitable interfaces can be set up for this purpose. Basically, the intervention of experts for spectroscopic analysis is unnecessary, even for evaluating a reference spectrum. In this respect, it is also possible to have the user measure new reference spectra and use them immediately in the method according to the invention. Preferably, for this purpose, the spectroscopy apparatus is not only designed for data evaluation but also for data gathering.

Further advantages of the invention can be seen from the detailed description and the drawings. Likewise, according to the invention, the characteristics stated above and the characteristics explained further can in each case be applied individually in their own right or jointly in any combination. The embodiments shown and described are not to be understood as a conclusive list, but rather they have an exemplary character for illustrating the invention.

BRIEF DESCRIPTION OF THE DRAWINGS

FIG. 1 shows various spectra associated with electronic spiking of alanine in energy drink spectra, in which alanine has two signals at 1.50 ppm:
  Bottom Spectrum: Spectrum without alanine.
  Middle and Top Spectra: Spectra with alanine in different concentrations;
FIG. 2A shows a relative error as a function of concentration in a first iteration step of the method described herein.

DETAILED DESCRIPTION

Figure 2B:
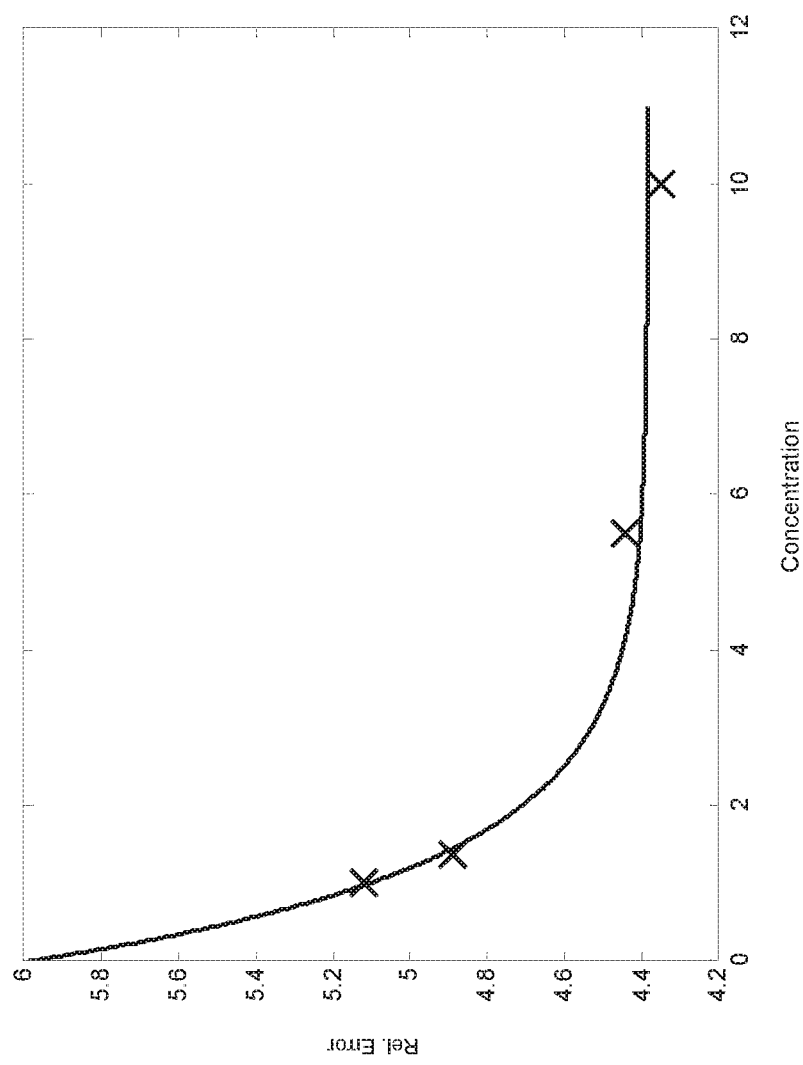
FIG. 2B shows a relative error as a function of concentration in a second iteration of the method described herein.

The method of the invention is further described below with reference to a specific application example.
  Task: Quantification of alanine in energy drinks
  Measuring method: NMR spectroscopy
  Question: "Above what concentration is the calculated value sufficient?"
  Objective: Determination of the LOQ at a relative error of $E_B=5\%$
  Maximum difference from target accuracy (tolerance range): 0.01%
  FIG. 1 shows three different spectra arranged one below the other with electronic spiking of alanine in an energy drink.
  Alanine has two signal sub-spectra. The region around 1.5 ppm is used, as the region around 4 ppm is strongly overlaid.
  Bottom: Without alanine
  Middle and top: Alanine in different concentrations.
  Conventional Method According to the Prior Art in the AssureNMR Software (See Reference [4]):
  The pure blank spectrum is used first. The alanine signal is not detected here. In the next step, a concentration of 1 mmol/l is assumed. "Electronic spiking" is now carried out:
    1. A measured alanine spectrum is multiplied by a factor, thus resulting in a concentration of 1 mmol/l for this spectrum.
    2. This alanine spectrum is added to the blank spectrum.
  This artificial spectrum is used to quantify alanine. The expected value was 1 mmol/l; the calculated value was 1.051197. The relative error is 5.1197% and is therefore greater than 5%.

In order to arrive at a concentration with an error <5%, the last value is multiplied by a positive factor, in this case by 10. An "electronic spiking" spectrum is also generated for this concentration and a quantification subsequently carried out. Here, the relative error is 4.3499% and is less than the target accuracy.

The binary search begins in the next step: the new concentration is calculated as the mean value of the lowest concentration<5% error (10 mmol/l) and greatest concentration>5% error (1 mmol/l). This results in a concentration of 5.5 mmol/l in this step. The use of electronic spiking and quantification results in a relative error of 4.4444%.

The iteration is carried out further; the table below shows the results of the further steps.

| Concentration | Rel. error |
|---|---|
| 0.0 | <limit of detection |
| 1.0 | 5.11967915767173 |
| 10.0 | 4.349932405998693 |
| 5.5 | 4.444416288701125 |
| 3.25 | 4.493444332420989 |
| 2.125 | 4.653167885874677 |
| 1.5625 | 4.819343640982979 |
| 1.28125 | 4.956825968990447 |
| 1.140625 | 5.045404570934175 |
| 1.2109375 | 5.000305382343138 |

The LOQ is determined to be 1.21 mmol/l; here, at 5.0003%, the relative error is less than the sought-for tolerance. A total of 10 steps were required.

Method According to the Invention:

As the relative error becomes smaller with increasing concentration, the model function must be monotonically decreasing. Concentrations vary in the range of positive real numbers including 0. At a concentration of 0, the relative error is infinite. Exponential functions fulfill these requirements.

In this example, an exponential function is chosen as the model function:

$$F(c)=a*e^{(b*c)}+d$$

In practice, this function usually returns sufficiently good values. An example of an alternative function is $F(c)=a*e^{(b*c)}+d*e^{(e*c)}+f$. This function returns somewhat more accurate results but requires considerably longer computation times due to its five parameters.

The chosen model function has 3 parameters, which must be adapted, as a result of which 3 start concentrations with associated relative errors are required for the first iteration. Start concentrations are taken from the expected concentration range, wherein one is chosen to be very small in order to be able to adapt the function more quickly. In practice, a value of 1 mmol/l has proved to be beneficial. If the substance is not detected at this value, the concentration is multiplied by a factor of 10 until the substance is detected. The value is then halved, for example, until the necessary number of start parameters has been determined.

In this example, the values 1, 5.5 and 10 mmol/l are used, similar to the example above, in order to guarantee comparability of the methods.

If these values are used (see table above) to iteratively adapt the model function to the values using a -Levenberg-Marquardt algorithm using the principle of mean square deviation, this results in the following parameters:

a=1.215; b=−0.437; d=4.335

FIG. 2A shows the result of this first iteration step.

To calculate the new target concentration, the model function is converted:

$$c=\ln((F(c)-d)/a)/b,$$

where the expected error of $E_B$=5% is used for F(c).

This gives the new concentration of 1.3792 mmol/l, 4.89% relative error.

A further iteration with 4 pairs of values now gives a=1.605; b=−0.7958; d=4.384

FIG. 2B now shows the result of the second iteration step. This results in a new concentration of 1.2034 mmol/l.

"Electronic spiking" and subsequent quantification results in a relative error of 5.0048%, whereby the value lies within the required tolerance of 0.01%.

With the method of the prior art, 10 quantifications must be carried out; with the method according to the invention, only 5.

A further advantage is that, by applying the calculated error function, the relative error for the current concentration can now be definitively predicted in a given measurement.

Figure 3:
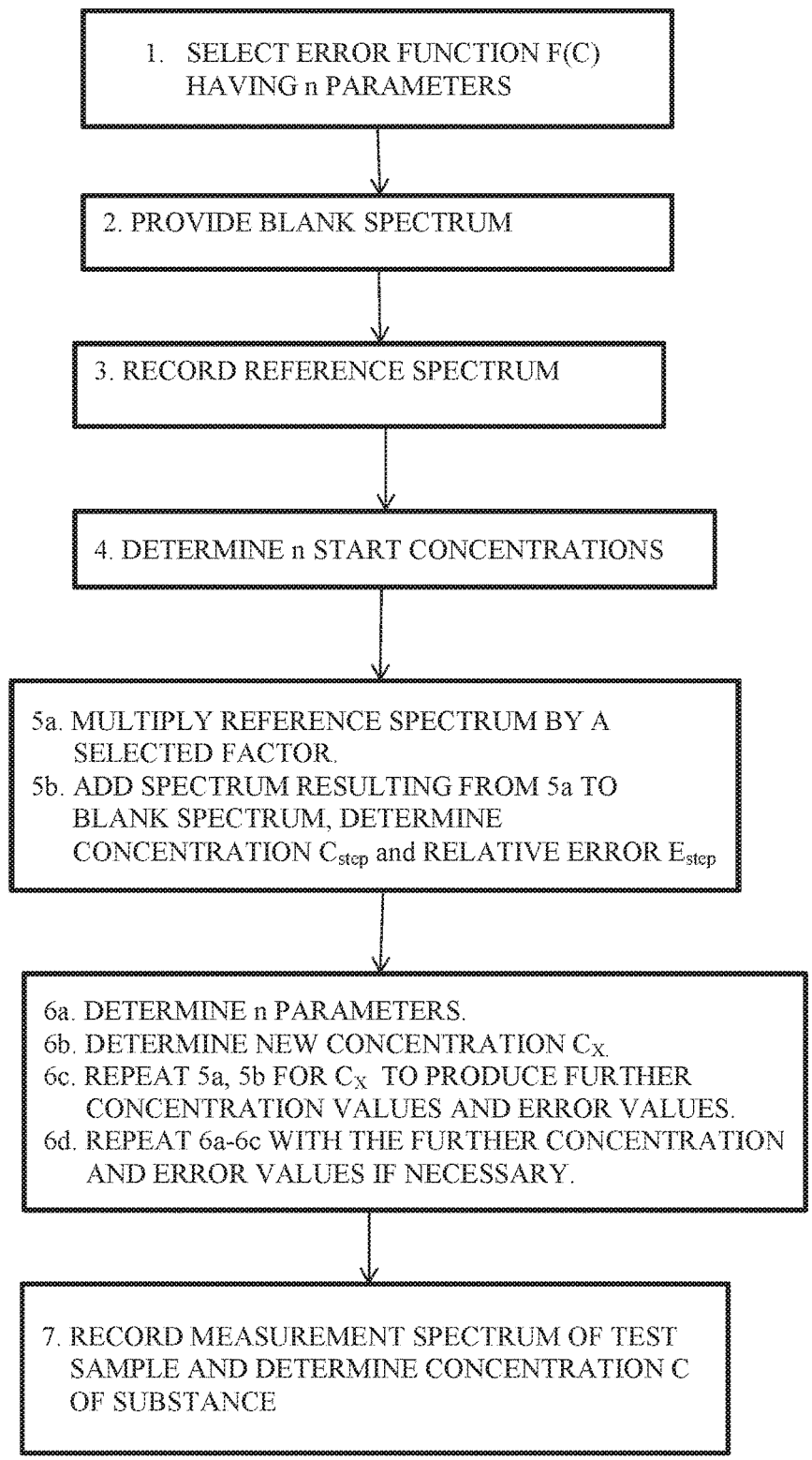
FIG. 3 is a flowchart of method steps according to an embodiment.

FIG. 3 is a flowchart showing steps 1-7 of the method of the invention as described above at a summary/high-level. That is, FIG. 3 represents a spectroscopic method for determining a limit of quantification (LOQ) and for determining a relative error when quantifying a concentration C of a substance to be investigated in a test sample.

Step 1 includes selecting the error function F(C) having n parameters.

Step 2 includes providing the blank spectrum.

Step 3 includes recording the reference spectrum.

Step 4 includes determining n start concentrations.

For each start concentration, step 5 (including steps 5a and 5b) is repeated. Step 5a includes multiplying the reference spectrum by a selected factor. Step 5b includes adding the spectrum resulting from the multiply to a blank spectrum and determining a concentration $C_{step}$ and a corresponding relative error $E_{step}$.

Step 6 includes iteratively adapting the n parameters by performing the following intermediate steps:

6a. determining the n parameters based on the previously determined relative error $E_{step}$ for each corresponding concentration $C_{step}$;

6b. determining a new concentration $C_x$;

6c. repeating steps 5a and 5b for $C_x$ to calculate a further concentration value and error value; and 6d. repeating steps 6a-6c with the further concentration and error values if necessary; and Step 7 includes recording a measurement spectrum and determining the concentration C of the substance to be investigated.

REFERENCES

[1] Ermer, Joachim; Miller, John (Editor), Method Validation in Pharmaceutical Analysis, Wiley-VCH, Weinheim, 2005.
[2] DE 10 2014 203 721 A1.
[3] Munecy, H. et.al, MetAssimulo: Simulation of Realistic NMR Metabolic Profiles, BMC Bioinformatics 2010, 11:496 doi:10.1186/1471-2105-11-496.
[4] Bruker Software "AssureNMR," published on the Internet https://www.bruker.com/fileadmin/user_upload/8-PDF-Does/MagneticResonance/Events_NMR/ENC2015/Posters/17_ENC15_Assure-lores.pdf.

What is claimed is:

1. A spectroscopic method for determining a limit of quantification LOQ and for determining a relative error E when quantifying a concentration C of a substance being investigated in a test sample using a spectroscopy apparatus, wherein the limit of quantification LOQ specifies the concentration C of the substance at which the relative error E becomes less than a specified value $E_B$, and wherein, in a measured spectrum, an intensity is determined as a function of a position of a signal component which is ascribed to the substance, comprising:

(1) selecting an error function F(C) which specifies how the relative error changes with the concentration C of the substance and which is dependent on n parameters;

(2) providing a blank spectrum;
(3) recording a reference spectrum having the signal component corresponding to the substance being investigated;
(4) determining at least n start concentrations $C_i^0$ (i=1 . . . n) of the substance;
(5) for each start concentration $C_i^0$:
  (a) multiplying the reference spectrum having the signal component of the substance by a factor selected such that the signal component corresponds to the concentration C of the substance; and
  (b) adding a spectrum resulting from said step (5)(a) to the blank spectrum provided in said step (2), determining a concentration $C_{step}$ of the substance resulting from said multiplying step 5(a), and calculating a relative error $E_{step}$;
(6) iteratively adapting the parameters of the error function F(C) by performing the following intermediate steps:
  (a) determining the n parameters of the error function F(C) based on the relative errors $E_{step}$ previously determined in said step (5)(b) for each corresponding concentration $C_{step}$;
  (b) determining a new concentration value $C_x$, wherein the error function F(C) with the parameters determined in said intermediate step (6)(a) is used to calculate the concentration value $C_x$ at the specified value $E_B$ of the relative error E;
  (c) performing the following steps for the concentration $C_x$ determined in step 6(b):
    (i) multiplying the reference spectrum by the signal component of the substance by a factor selected such that the signal component corresponds to the concentration $C_x$ of the substance;
    (ii) adding a spectrum resulting from step (i) to the blank spectrum provided in step 2, and determining a concentration $Cx^{step}$ of the substance and determining a relative error $Ex^{step}$; and
  (d) x times (x=1, 2, . . . ) repetition of the intermediate steps (6)(a) to (6)(c) using values determined for a concentration $Ci^{step}$ and a relative error $Ei^{step}$ from each of the starting concentrations $Ci^{step}$ and additionally the x determined values for the concentration of the substance $Cx^{step}$ and the relative error $Ex^{step}$ until, for the value of the concentration $Cx^{step}$ determined in the xth iteration, the determined value of the relative error E is within a tolerance range of the predetermined determination limit specified value $E_B$.

2. The method according to claim 1, wherein the error function is given by F(C)=a*exp(b*C)+d, where a, b and d are constants, C represents the concentration and F(C) the relative error.

3. The method according to claim 1, wherein said step (2) includes providing a spectrum of a blank sample which does not contain the substance, or a theoretical noise spectrum, or a spectrum of a test sample being investigated which also contains the substance being investigated, wherein the concentration C of the substance in the test sample is predetermined and a signal content of the substance is subtracted from the spectrum.

4. The method according to claim 1, wherein said step (2) includes providing a plurality of blank spectra, and, wherein a maximum of individual deviations or some other error quantile is used as the relative error $E_{step}$ to optimize the error function F(C).

5. The method according to claim 1, further comprising varying positions of the signal component by shifting the reference spectrum between said steps (5)(a) and (5)(b).

6. The method according to claim 5, further comprising determining a dedicated error function and correspondingly the limit of quantification for each of the signal positions.

7. The method according to claim 3, further comprising, when using a plurality of blank samples, classifying the blank spectra in advance of performing said steps (1)-(6) to produce corresponding classes, and determining an error function for each class of the classes in order to enable a class-specific processing of new samples.

8. The method according to claim 1, wherein said step (3) includes measuring the signal component of the substance being investigated by using a measured reference spectrum or by using a simulation.

9. The method according to claim 7, wherein, instead of adding the signal component to the blank spectra electronically in said steps (5)(a) and (5)(b), the substance being investigated is mixed and measured with the blank samples.

10. The method according to claim 1, wherein determining the relative error E of the test sample includes dividing the error function into different substance concentration ranges including a relatively lower substance concentration range and a relatively higher substance concentration range and using a linear error function F(C) for the relatively higher substance concentration range.

11. The method according to claim 1, further comprising calculating a limit of detection LOD, wherein the limit of detection specifies a concentration above which the substance being investigated can be identified.

12. The method of claim 1, further comprising recording a measurement spectrum of the test sample and determining the concentration C of the substance being investigated by performing the adding, the determining, and the calculating of said step (5)(b) using the measurement spectrum of the test sample, comparing the concentration C with the limit of quantification LOQ corresponding to the relative error E and calculating the relative error E by applying the error function F(C) from said step (6).

* * * * *